(12) United States Patent
Altamar et al.

(10) Patent No.: US 8,974,820 B2
(45) Date of Patent: *Mar. 10, 2015

(54) APPARATUS AND PROCESS FOR ENCAPSULATING MICROPARTICLES WITH LIQUID IN SOFT GEL CAPSULES

(75) Inventors: Carlos Salazar Altamar, Barranquilla (CO); Gustavo Anaya, Soledad (CO); Braulio Teran, Barranquilla (CO); Newman Aguas Navarro, Barranquilla (CO); Willmer Herrera, Barranquilla (CO)

(73) Assignee: Procaps SAS, Barranquilla (CO)

( * ) Notice: Subject to any disclaimer, the term of this patent is extended or adjusted under 35 U.S.C. 154(b) by 97 days.

This patent is subject to a terminal disclaimer.

(21) Appl. No.: 13/137,051

(22) Filed: Jul. 18, 2011

(65) Prior Publication Data
US 2012/0058179 A1 Mar. 8, 2012

Related U.S. Application Data

(60) Provisional application No. 61/344,417, filed on Jul. 19, 2010.

(51) Int. Cl.
| | | |
|---|---|---|
| A61K 9/64 | (2006.01) | |
| A61K 9/48 | (2006.01) | |
| A61K 9/52 | (2006.01) | |
| A61K 9/54 | (2006.01) | |
| A61K 9/56 | (2006.01) | |
| A61K 9/58 | (2006.01) | |
| A61K 9/60 | (2006.01) | |
| A61K 9/62 | (2006.01) | |
| A61J 3/07 | (2006.01) | |

(52) U.S. Cl.
CPC ............... *A61J 3/07* (2013.01); *A61K 9/4808* (2013.01); *A61K 9/4883* (2013.01)
USPC ........... 424/456; 424/455; 424/458; 424/451; 424/452; 424/459; 424/460; 424/461; 424/462

(58) Field of Classification Search
None
See application file for complete search history.

(56) References Cited

U.S. PATENT DOCUMENTS

| | | | | | |
|---|---|---|---|---|---|
| 1,970,396 | A | * | 8/1934 | Scherer | 53/451 |
| 2,774,988 | A | * | 12/1956 | Stirn et al. | 425/223 |
| 4,174,054 | A | * | 11/1979 | Hubbard | 222/241 |
| 5,350,597 | A | * | 9/1994 | Pelley | 427/197 |
| 2004/0151777 | A1 | * | 8/2004 | Ayers et al. | 424/490 |
| 2006/0078622 | A1 | * | 4/2006 | Majuru et al. | 424/489 |

* cited by examiner

*Primary Examiner* — Isis Ghali
(74) *Attorney, Agent, or Firm* — Isaac A. Angres

(57) ABSTRACT

The invention provides an apparatus for producing soft gel capsules having encapsulated therein microparticles, nanoparticles and fluids, said apparatus comprising: (a) two spreader boxes; (b) two casting drums; (c) a pair of rotary dies; (d) a liquid fill system (medicine pump system); (e) a wedge for heating gelatine ribbons and feeding said fill; and (f) one or more microgranule or nanogranule feeders located on each side of the rotary dies, said feeders being synchronized to rotate at the same tangential speed as the rotary dies.

10 Claims, 6 Drawing Sheets

Figure 1:
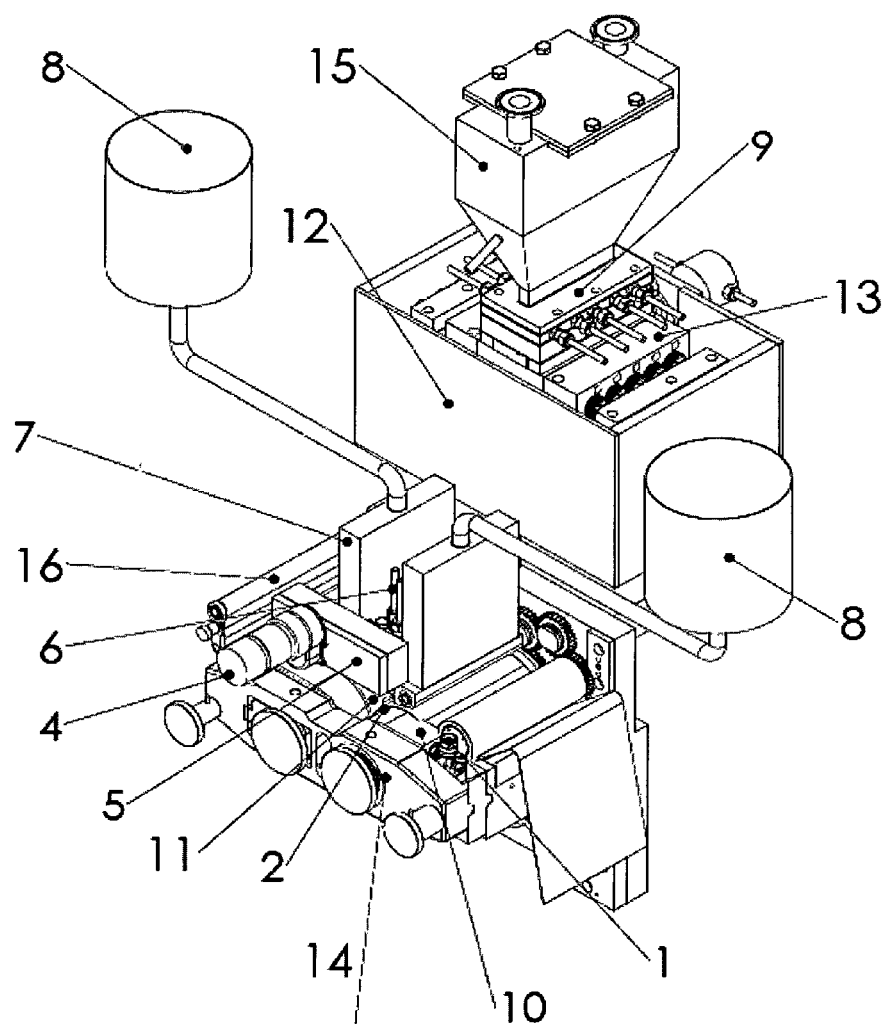

APPARATUS AND PROCESS FOR ENCAPSULATING MICROPARTICLES WITH LIQUID IN SOFT GEL CAPSULES

This application claims the priority benefit under 35 U.S.C. section 119 of U.S. Provisional Patent Application No. 61/344,417 entitled "Apparatus And Process For Encapsulating Microparticles With Liquid In Soft Gel Capsules" filed Jul. 19, 2010, which is in its entirety herein incorporated by reference.

FIELD OF THE INVENTION

The present invention generally relates to a gelatin capsule of soft type containing medicine or the like, and more particularly to a novel gelatin capsule capable of containing powders, microparticles, nanoparticles or time release pellets as the content, and its manufacturing method and manufacturing apparatus.

This invention relates to methods and apparatus for the production of soft gelatin capsules containing particulate material such as microparticles or nanoparticles. Such capsules are now well established in the marketplace as a means for providing a variety of liquid products such as drugs and dietary supplements in a readily ingestible form.

This invention further relates to softgels (or soft gelatin capsules) and to a process and apparatus for the manufacture thereof. The present invention also relates to a gelatin capsule of the soft type containing medicine or the like, and more particularly to a novel gelatin capsule capable of containing medicinal or dietary supplement microparticles or nanoparticles as the content, and its manufacturing method and manufacturing apparatus.

The present invention also relates generally to a method and apparatus for forming capsules containing a measured amount of microparticles or nanoparticles and microparticles or nanoparticles with liquid fill material, and more particularly to a method and apparatus for forming capsules from webs or sheets of capsule forming material, such as gelatin, as well as to various features of such method and apparatus, including an apparatus for forming webs for use in such capsule making method and apparatus. The method and apparatus of the present invention are particularly useful in connection with forming softgel capsules containing a pharmaceutical product, such as for example medicines, vitamins, food supplements and the like.

The instant invention also relates to apparatus for producing filled gelatin capsules comprising rotary dies or rollers having recesses against which the capsule wall is shaped. Such rotary die apparatus comprises two cylindrical rollers mounted with their longitudinal axes substantially parallel and defining a nip therebetween. A plurality of recesses are formed in the outer surface of at least one of the rollers, and means are provided for feeding gelatin ribbon to each roller surface and thereby to the nip.

The present invention further relates to encapsulation machines and, more particularly, to soft encapsulation machines which make soft gelatin and non-gelatin capsules containing micro-particles and nanoparticles, especially said particles in suspension or dispersion forms.

BACKGROUND OF THE INVENTION AND DESCRIPTION OF THE PRIOR ART

The art of encapsulation has been known for many years, particularly for the production of unit dosage forms containing various pharmaceutical products. Normally, such pharmaceutical capsules are composed of gelatin or some modification thereof, which is fabricated essentially into two different forms, namely, the so-called hard gelatin capsule and the soft gelatin capsule.

It is also known that conventional soft gelatin capsules are a preferred from of administration for medicaments and similar products; especially liquids, pastes, solids dispersed in liquids, or dry solids. Soft gelatin capsules also possess particular advantages for substances which require total protection from air and light, because the gelatin is completely sealed around the contents. An important example is for the encapsulation of vitamins, which has resulted in a high degree of stability thereof.

Hard gelatin capsules are also known in the art, and are generally formed from two distinct parts, namely the "cap" and the "body", fitting one into the other so as to form the complete capsule. The cap and the body are manufactured by the same process consisting of immersing in a gelatin solution the end of a mandrel whose form corresponds to the inner volume of the cap or of the body, then withdrawing the mandrel from the solution and letting the layer of gelatin thus deposited dry, which is then removed like a glove finger. Hard shell capsules so formed have problems of leakage and do not provide adequate protection from air and light Soft gelatin capsules, now more commonly known as softgels, have been well known and widely used for many years. Softgels generally comprise an outer shell primarily made of gelatin, a plasticizer, and water, and a fill contained within the shell. The fill may be selected from any of a wide variety of substances that are compatible with the gelatin shell. Softgels are widely used in the pharmaceutical industry as an oral dosage form containing many different types of pharmaceutical and vitamin products. In addition to use as an oral dosage form for drugs and vitamins, soft gelatin capsules or softgels are also designed for use as suppositories for rectal or vaginal use. Other uses are for topical and ophthalmic preparations and the like. The cosmetic industry also uses softgels as a specialized package for various types of perfumes, oils, shampoos, skin creams and the like. Softgels are available in a great variety of sizes and shapes, including round shapes, oval shapes, oblong shapes, tube shapes and other special types of shapes such as stars. The finished capsules or softgels can be made in a variety of colors. Also, opacifiers may be added to the shell.

The process for making softgel capsules includes the step wherein the gelatin shell and the fill material come together to form Softgel capsules. It takes place in a closed environment called clean room where the relative humidity is around 20%. The gelatin shell and fill material are brought together simultaneously in the encapsulation machine.

The process is basically performed as follows: a pump delivers the warm gelatin over two chilled drums which are located at both opposite sides of the machine, through a spreader box that sits over each drum. The warm liquid gelatin flows over the drums and this transforms the liquid gelatin into two solid ribbons of gel. The left and right ribbons pass over rollers which feed them through two die rolls. These die rolls determine the shape and size of softgels and cut the Softgel shell from the ribbons as they turn around.

Simultaneously, a sensitive and high accuracy positive displacement pump delivers the fill material into a heated wedge which sits between rotary dies. This wedge injects the fill material into the die cavities between ribbons just right before the die rolls cut the ribbons and seal the two halves together. Warm just formed softgels slide gently through a chute onto a conveyor belt which carries them to the tumble dryer where cooling and drying process takes place.

In more specific detail, typical soft encapsulation machines form at least two flexible gelatin sheets or ribbons by cooling molten gelatin on separate drums then lubricating and guiding the sheets into communication with each other over co-acting dies while simultaneously dispensing a desired quantity of fill material between the sheets in synch with cavities in the outer surfaces of the dies to produce soft capsules. The encapsulation machines typically utilize gearing to control the relative rotations of the various components and fill mechanisms to synchronize the operation of these various components. The synchronization of these various components, however, can vary depending upon a variety of factors, such as the particular dies used, the number of cavities and the size of the cavities on the dies, and the type of material used to form the sheets. To change the synchronization of the various components, mechanical gears are required to be changed to obtain the desired ratios and synchronization of these components. The changing of gears, however, is time intensive. Additionally, the use of mechanical gears provides finite gear ratios which limit the synchronization of the various components to the mechanical gears that are available. Thus, it would be advantageous to provide a capsule machine wherein the synchronization and rates at which the various components operate can be altered without the necessity of changing gears. Additionally, it would be advantageous if the synchronization between the various components can be infinite to thereby allow more precise synchronization between the various components. It would also be advantageous to allow various components, such as the fill mechanism, to be adjusted independently of the other components while the machine is running to allow for adjustments of the timing of fill material inserted into each of the soft capsules.

During the operation of the capsule making machine, the contact between the adjacent dies can be adjusted by the operator of the capsule making machine. Typically, the operator is able to move one of the dies closer to the other die so that the pressure or force exerted on the sheets passing between the adjacent dies can be adjusted. Such adjustments, typically are mechanical adjustments made by fluid actuators, such as pneumatic cylinders. The operator is able to adjust the pneumatic pressure thereby altering the force the dies exert on one another and on the sheets. This adjustability allows an operator to customize the pressure to ensure that quality soft capsules are produced. However, the dies are susceptible to premature failure and/or wear when the pressure or force between the two dies is more than that required to produce acceptable soft capsules. Thus, it would be advantageous to monitor/record the pressure applied to the dies so that quality capsules are produced without inducing excessive wear or premature wear on the dies.

A material fill mechanism is used to supply the fill material that is encapsulated within the soft capsules. When the fill material is a liquid, such as a liquid medication or die for a paint ball capsule, the fill mechanism includes a plurality of positive displacement plunger-type pumps that are arranged in a housing above the dies. The plunger-type pumps are positioned on a yoke that moves linearly in a reciprocating motion to allow the plunger-type pump to fill with the liquid fill material on one stroke and subsequently discharge the liquid fill material on the other stroke. A valving arrangement between opposing pumps is utilized to control the discharge and filling of the pumps. The valve arrangement includes a sliding member that moves linearly back and forth in a direction generally perpendicular to the linear motion of the yoke. The discharge of the liquid fill material into the sheets as they are passing through the dies is coordinated with the operation of the dies to insure that the timing of the injection of the liquid fill material is synchronized with the cavities on the dies. Typically, this synchronization has been performed through the use of mechanical gears that link the timing of the stroke to the rotation of the dies. Thus, in order to adjust the synchronization a mechanical gear change is required which is time consuming. Additionally, the timing is limited to a finite number of gear ratios as determined by the gears that are available.

The sliding member of the valving mechanism requires lubrication. Typically, the lubrication is provided by a lubricating pump with its own separate drive. However, the use of a separate drive to operate the lubricating pump adds additional complexity and components to the capsule machine. Thus, it would be advantageous if a motion of the slide member and/or the yoke could be utilized to drive the lubrication pump.

The pumps are typically contained within a housing that is filled with a lubricating oil that is used to lubricate the sliding member. The pumps, however, can leak around their seals and contaminate the lubricating oil with the leaking fill material. Contamination of the oil requires a time consuming and possibly difficult clean up and can cause the lubricating oil to not perform as designed thereby increasing the wear on the sliding surfaces and decreasing the life span of the sliding surfaces. Thus, it would be advantageous to capture any fill material that leaks from the pumps and deter or prevent the liquid fill material from contaminating the lubricating oil within the pump housing.

The pumps are typically driven by a drive mechanism that is also located within the pump housing. Because the drive mechanism is located in the pump housing, it is possible for liquid fill material that leaks from the pumps to contaminate not only the lubrication oil but also the drive mechanism. When switching from one fill material to another, the pump and all of the components in the pump housing are required to be thoroughly cleaned to remove all contamination. The locating of the drive mechanism within the pump housing provides additional components that must also be cleaned when changing the fill material. Thus, it would be advantageous to separate the drive mechanism from the pump housing to reduce the components that are required to be cleaned when changing fill material.

The soft capsules produced by the encapsulation machine are transported from the encapsulation machine to a dryer to additionally dry the soft capsules and to make them into final form. The soft capsules are transported from the encapsulation machine to the dryer by a conveyor that extends along the front of the encapsulation machine. The conveyor can be contaminated by the fill material during operation of the encapsulation machine. When it is desired to switch the product being produced on the encapsulation machine, the conveyor must be removed from the encapsulation machine and cleaned to remove any contaminates thereon. The conveyor is driven by a motor that is attached to the conveyor. When it is necessary to remove the conveyor for cleaning, the motor must also be taken with the conveyor which makes it more difficult to remove and transport the conveyor and requires additional time to disconnect the motor from the encapsulation machine. Thus, it would be advantageous to provide a conveyor that can be easily and quickly disconnected from the motor and removed from the encapsulation machine without the motor. The present invention provides an encapsulation machine that overcomes the above-described disadvantages of typical encapsulation machines.

Thus, it would be advantageous to provide a fill mechanism that is synchronized with the dies without the use of a mechanical linkage. Additionally, it would be advantageous if such synchronization could be adjusted during operation of the encapsulation machine to fine tune the synchronization and the production of capsules.

Applicant is aware of the following publications briefly discussed below. U.S. Pat. No. 1,970,396 features a method and machine for producing soft gelatin capsules in an automated process. The method involves the formation of two gelatin sheets or films through the use of a gravity fed spreader box, cooling the liquid gelatin on two separate webs, then lubricating and guiding the two sheets into communication with each other between two co-acting dies while simultaneously dispensing the proper amount of medicine or other filling material between the sheets in registration with half cavities in the outer surface of the dies.

U.S. Pat. No. 5,761,886 discloses an apparatus for forming capsules that provides rotary dies that are independently moveable and the ability to vary the speed of the dies during the formation of a single capsule. The '886 device also utilizes independently controlled casting drums to reduce "set-up" time and provide better quality control. Even though the '886 patent discloses a very sophisticated encapsulation machine, it still utilizes a gravity fed spreader box for formation of the encapsulating ribbon.

Other patents relating to encapsulation techniques which disclose the use of spreader boxes to create the film or ribbon on a casting drum include U.S. Pat. Nos. 2,288,327; 2,774,988; 5,246,638; 5,735,105; and 6,022,499.

SUMMARY OF THE INVENTION

The invention provides an apparatus for producing soft gel capsules having encapsulated therein microparticles, nanoparticles and fluids, said apparatus comprising: (a) two spreader boxes; (b) two casting drums; (c) a pair of rotary dies; (d) a liquid fill system (medicine pump system); (e) a wedge for heating gelatine ribbons and feeding said fill; and (f) one or more microgranule or nanogranule feeders located on each side of the rotary dies, said feeders being synchronized to rotate at the same tangential speed as the rotary dies.

The invention further provides a method for forming soft-gel capsules having incorporated therein microgranular or nanogranular materials, powders and granular materials or powders dispersed in a suitable liquid, said method comprising: (a) feeding film sheets between a first rotary die and a second rotary die wherein each of the rotary dies have capsule pockets in a plurality of rows and said capsule pockets have at least one orifice for application of suction; (b) applying suction while said film is in place in the capsule pockets; (c) applying said granular material or powders or granular materials or powders dispersed in a suitable liquid onto the film sheets overlying the rotary dies at positions having the capsule pockets through a feeding mechanism located on each side of the rotary die; and (d) cutting the film sheets about the capsule pockets to form said soft gel capsules having granular material or powders or granular materials or powders dispersed in a suitable liquids.

The invention further provides an apparatus for producing soft plastic or gelatinous capsules filled with a microgranules or nanogranules dispersed in a liquid, comprising: (a) on or more spreader boxes; (b) one or more casting drums, (c) a means for feeding a strip of soft plastic or gelatinous material sheets between a first rotary die and a second rotary die wherein each of the rotary dies have capsule pockets in a plurality of rows; (d) a vacuum means for causing said strip of soft plastic or gelatinous material to be pulled in tight against the walls of the capsule forming cavities; (e) a means for filling said cavities with liquid and microgranules or nanogranules composition; (f) a means for sealing the filled cavities; and (e) an ejection means for removing the sealed filled capsules from said rotary dies.

DETAILED DESCRIPTION OF THE INVENTION

The following description is merely exemplary in nature and is in no way intended to limit the invention, its application, or uses.

As used herein the term "gelatin" means gelatin and derivatives thereof. It is also understood to include other proteins similar to gelatin in physical and chemical properties and gelatin combined with starch or derivatives thereof. Gelatins are generally obtained by the partial hydrolysis of collagen derived from the skin, white connective tissues and bones of animals. Gelatin derived from an acid-treated precursor is known as type A and exhibits an isoelectric point between pH 7 and pH 9, while gelatin derived from an alkali-treated precursor is known as type B and exhibits an isoelectric point between pH 4.7 and pH 5.2. Capsules made of gelatin may be colored. See Remington's Pharmaceutical Sciences, Mack Publishing Co., 17th Edition, 1985, page 1298. Also contemplated by the present invention are any soft elastic capsules (SEC) which are generally described as soft, globular, gelatin shells. The gelatin is plasticized by the addition of glycerin, sorbitol, or a similar polyol. The soft gelatin is plasticized by the addition of glycerin, sorbitol, or a similar polyol. The soft gelatin shells may contain a preservative to prevent the growth of fungi. Commonly used preservatives are methyl- and propylparabens and sorbic acid. Where the suspending vehicle or solvent can be an oil, soft gelatin capsules provide a convenient and highly acceptable dosage form. The soft gelatin capsules can be prepared in a wide variety of shapes and sizes; they may be round, oval, oblong, tube or suppository shaped. Oral SEC dosage forms are generally made so that the heat seam of the gelatin shell opens to release its medication into the stomach less than five minutes after ingestion. When used as suppositories, it is the moisture present in the body cavity that causes the capsule to come apart as its heat-sealed seam and to release its contents. See Remington's Pharmaceutical Sciences, Mack Publishing Co., 17th Edition, 1985, page 1029.

A great variety of products may be encapsulated in soft gelatin capsules according to the present invention. Among these are medicinal compounds such as drugs or vitamins. The capsules of the present invention may also be employed in food packaging, such as for powdered instant coffee or spices; candy manufacturing; fertilization of ornamental plants and/or indoor plants; packing of sensitive seeds in combination with protective agents and/or fertilizers; and packing of single diestuffs or mixtures of various drugs. Capsules provide a convenient vehicle however small, accurately determined quantities of material are desired. It is contemplated herein to fill the capsules with a powder, granule, liquid or paste composition or even possibly a combination of such compositions.

The prior art machines typically comprises two rollers defining a nip therebetween, above which nip is mounted a wedge. The machines include an injection system for delivering liquid fill material to the nip as the rollers rotate. The gelatin ribbon (which is formed elsewhere) is delivered to each roller surface such that it is drawn into the nip from both sides as the rollers rotate.

In the prior art machines, each roller is formed with a plurality of hemispherical recesses defined at the roller surface by cutting edges or surfaces. In use, the rollers rotate in synchronism with each other such that the recesses are in registry at the nip, and with the injection system such that the liquid fill material is injected between the two gelatin ribbons when they are respectively located over the juxtaposed recesses. The injected fill material forces each length of gelatin ribbon away from the other and into the respective recess, until the capsule is closed by the coming together of the cutting edges and surfaces. The capsules are thus produced sequentially with a given length of laminated gelatin ribbon therebetween. The cutting edges and surfaces should have separated the lengths from the capsules, so that the capsules are produced individually.

In rotary die encapsulation machines of the kind explained above, each roller will normally have sufficient axial length to have a substantial number, for example at least twelve, recesses raised along its width. As a consequence, whereas the capsules are produced individually, the laminated ribbons take the form of a perforated sheet which can be drawn away as waste or for recycling.

The prior art machine described above is designed to create filled capsules containing liquids. We have developed a dispensing metered system which can be used in substantially similar encapsulation machines, and which can deliver metered quantities of liquids and at the same time also deliver metered quantities of microparticulate or nanoparticulate material to the nip between the gelatin ribbons. The systems of the invention are illustrated in FIGS. 1-6.

The present invention provides an apparatus and method for filling softshell gelatin capsules with microparticles, nanoparticles or a liquid in combination with microgranules or nanogranules. The invention also provides a system, apparatus and method for the manufacture of soft gelatin capsules having incorporated internally microparticles, nanoparticles, or a liquid in combination with microparticles and nanoparticles.

The method of the invention comprises depositing the microparticles or nanoparticles into the cavity that forms on top of the rotary dies before entering a segment tangentially. The gelatin fill cavity is formed by application of vacuum suction in the bottom of the pockets of the rotary die. The rotary die could have mold shapes such as oval, oblong, or round shapes. In each mold, while applying suction, the cavity is fed with a half dose of the microparticles or nanoparticles and at the time of sealing the capsule receives an amount of air needed to maintain it's shape.

The apparatus of the invention also includes a dispensing hopper which stresses the microparticles or nanoparticles for encapsulation. The dispensing hopper includes dispensing hoses to guide the microparticles or nanoparticles to the dosing devices that dispense said microparticles or nanoparticles.

The dosage dispensing device of the invention may be placed side by side of the wedge segment. Each of the dispensing devices provide half of the required dose. The dosing dispensers are driven by micromotors wherein their rpm will depend on the dose needed. This comprises a host located on the inside of the dosage dispenser, driven in part by another micromotor. The microparticles or nanoparticles enter the dispenser by its side through a hose that connects the hopper.

The vacuum system of the apparatus of the invention is responsible for generating the shape of the capsule through suction. In this system, one will adapt a vacuum, which will indicate the amount of suction that is needed. The suction system starts at 90 degrees in a counterclockwise direction in the second quadrant of the mold and ends at a position 180 degrees in the same quadrant. The wedged segment during this process will prevent the microparticles from escaping, leading them into the capsule at the tangential point of the two molds.

FIG. 1 of the invention shows a perspective view of the apparatus of the invention. The apparatus of the invention includes a vacuum system 1 for applying suction, a rotary die 2 (mold for capsule formation), a volumetric dispenser/feeder 3 for feeding microparticles or nanoparticles, a servomotor 4 for the synchronizing system, a box synchronizing system 5, a liquid injection system 6, a microgranule or nanogranule dispensing system 7, a hopper dispensing system 8 containing microparticles or nanoparticles, a pump 9 for injecting a liquid, vacuum chamber 10, a wedge 11, a holding box 12 for holding the pump that injects a medicine or other active materials, a dispensing pump 13, a holding system 14 for the rotary dies, a pharmaceutical active ingredient hopper and dispenser 15, and a gelatin film guiding roller 16.

Figure 2:
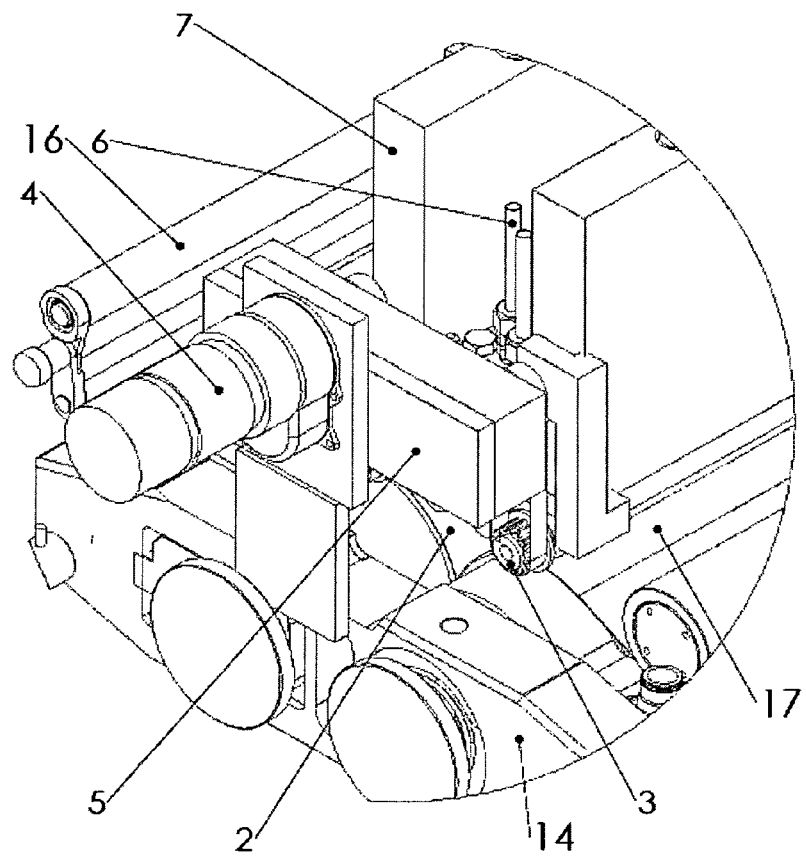

FIG. 2 is a more detailed view of the of the synchronizing system in combination with the dispensing system. FIG. 2 shows the rotary die 2, the volumetric dispenser 3, the servomotor 4 for the synchronizing box system 5, the liquid injection system 6, the microgranule or nanogranule dispensing system 7, the rotary die holding system 14, the gelatin film guiding system 16, and the rotary die 17.

Figure 3:
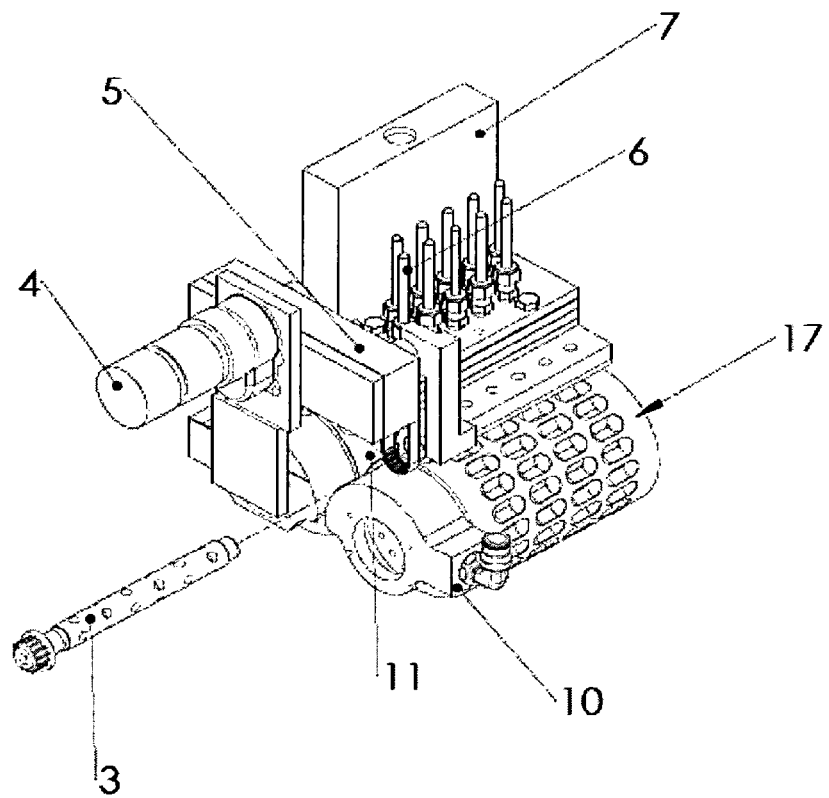

Referring to FIG. 3, there is a more detailed view showing the volumetric dispenser 3, the servomotor 4, the synchronizing system 5, the liquid injecting system 6, the microgranule or nanogranule dispensing hopper 7, the suction vacuum system 10, the wedge 11, and the rotary die 17.

Figure 4:
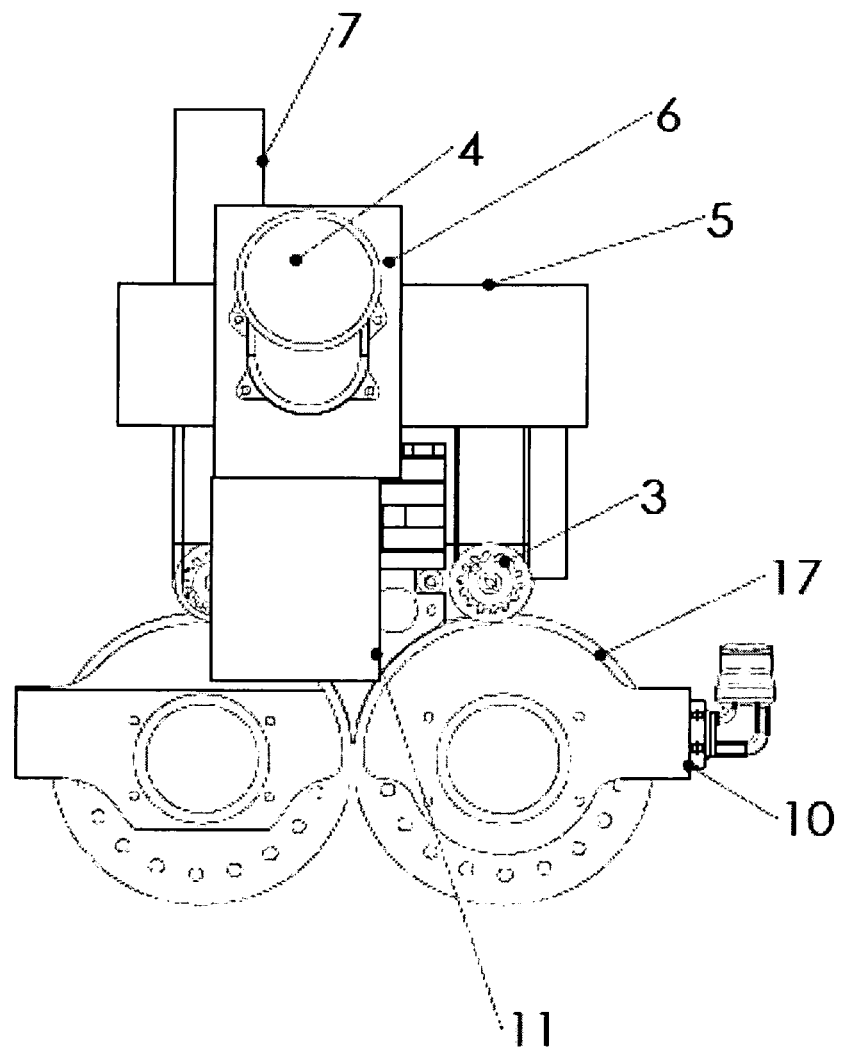

FIG. 4 shows another view featuring the volumetric dispenser 3, the servomotor 4, the synchronizing system 5, the liquid injecting system 6, the dispensing hopper 7 for the microparticles or nanoparticles, the vacuum system 10, the wedge 11, and rotary die 17.

Figure 5:
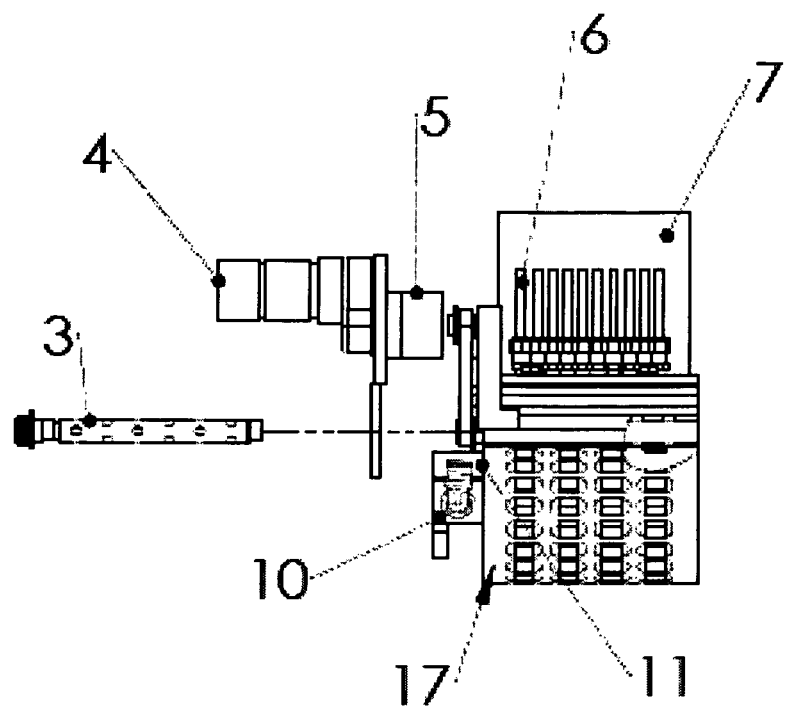

FIG. 5 is another perspective view of FIG. 4 showing the volumetric dispenser 3, the servomotor 4, the synchronizing system 5, the liquid injecting system 6, the dispensing hopper system 7 for the microparticles or nanoparticles, the vacuum system 10, the wedge 11 and the rotary die 17.

Figure 6:
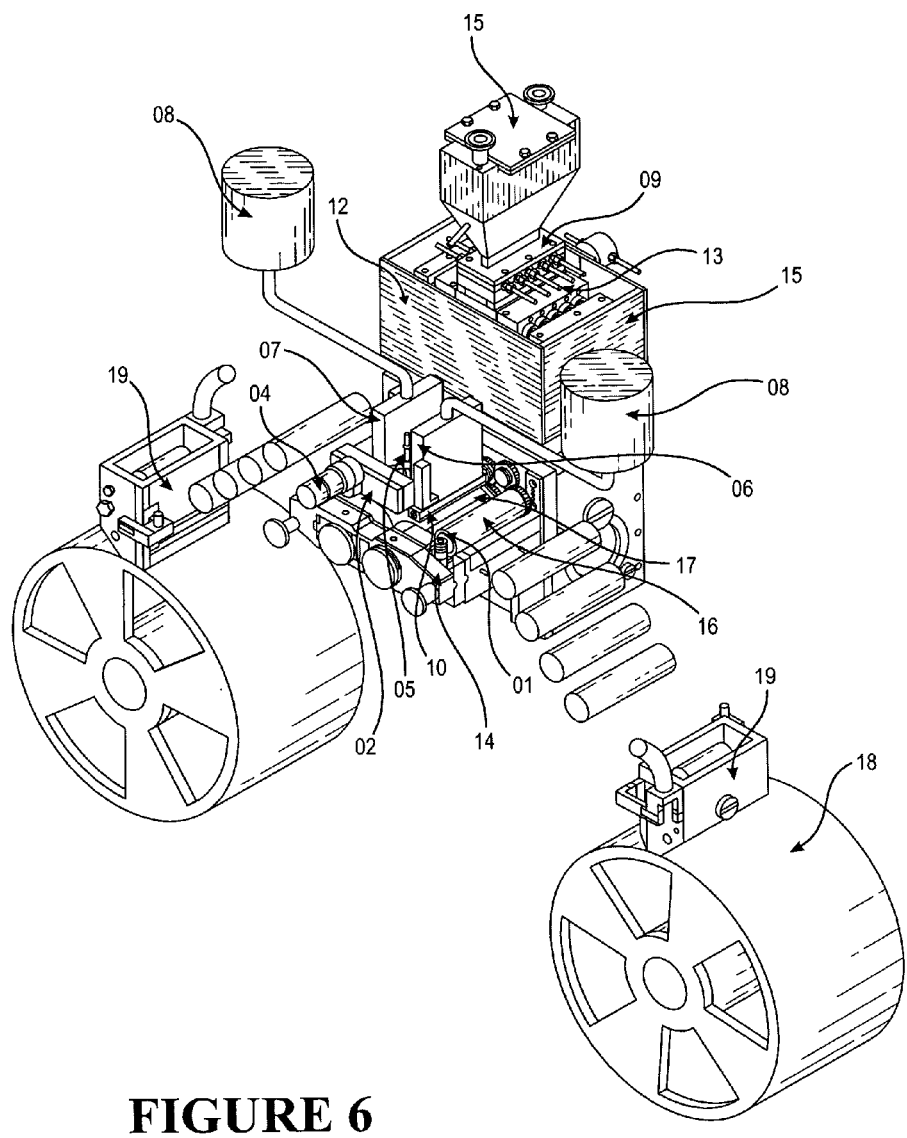

FIG. 6 is a full view of the apparatus shown in FIG. 1 which further describes the entire system including the spreader boxes 19 and the casting drum 18.

Additionally, according to the present invention there is provided a rotary die apparatus which includes a metering system for delivering microparticulate and nanoparticulate material between the gelatin ribbons at the nip. Means are also provided for rotating the rollers in a synchronized way with the dispensing and metering system, such that the microparticulate and nanoparticulate material is supplied over a recess in the roller or rollers to fill a capsule formed therein whereafter the juxtaposed ribbon sections close to seal it. Normally, each recess in one roller is in registry with a complementary recess in the other such that the eventually formed capsules are substantially globular.

The system and apparatus of the invention as shown in FIG. 1, includes means 1 for applying suction, a rotary die 2, a servomotor 4, a box synchronizing system 5, a liquid injection system 6, a microgranule or nanogranule dispensing system 7, a hopper dispensing system 8 containing microparticles or nanoparticles, a pump 9 for injecting a liquid, vacuum chamber 10, a wedge 11, a holding box 12 for holding the pump that injects a medicine or other active materials, a dispensing pump 13, a holding system 14 for the rotary dies, a pharmaceutical active ingredient hopper and dispenser 15, and a gelatin film guiding roller 16.

More specifically, FIG. 1 shows a front perspective view of the capsule making machine of the invention. The apparatus of the invention includes casting drums (not shown) on both sides of the machine. The fill hopper 15 is shown above the pump and pump housing 9. The gelatin ribbon (not shown)

starts out as liquid in a spreader box which maintains the gelatin in a liquid state using heat. The spreader box is typically gravity fed and places the gelatin melt on the casting drums using conventional techniques. The casting drum rotates and results in the formation of a continuous sheet or ribbon of gelatin. Cooling the molten gelatin on the casting drum creates a flexible gelatin ribbon which is threaded through guide roller assembly 16. An edible lubricant is typically placed on both sides of the ribbon to assist in the transfer of the ribbon to the rotary dies (not shown). Two ribbons are formed in the same manner using identical assemblies on either side of the machine (not shown). The gelatin ribbon formed on one drum provides the shell material for one side of the capsule. The rotary dies 2 are housed behind the yoke assembly (not shown). The gelatin ribbons are threaded over the co-acting dies (not shown) into communication with each other. Pressure is applied to the dies to force them against each other. This force, in conjunction with heat from the wedge assembly, causes the two ribbons of gelatin to be sealed together and cut along the cavities on the dies to produce a semi-formed, empty capsule. In simultaneous action, pump assemblies 9 and a volumetric feeder (not shown) for the microparticles or nanoparticles measures and dispenses the fill materials (i.e., nutritionals, pharmaceuticals and the like) through tubes into the injection wedge and then into the semi-formed, empty capsule via injection ports in the fill material distribution device or wedge. The rotation of the dies continues the sealing and cutting process to form a complete filled capsule.

Referring in greater detail to further aspects of the invention, a soft gel encapsulation machine according to the principles of the present invention is shown in FIGS. 1 and 6 while a schematic representation of a portion of the filling mechanisms is shown in FIGS. 2, 3, 4 and 5. The encapsulation machine is operable to produce soft gel capsules with a fill material containing a liquid having microparticles and nanoparticles suspended therein. The soft gel capsules produced by the encapsulation machine can be used for a variety of purposes. For example, the fill material can be a medicine in particulate form with a liquid and the soft capsules used to administer the medicine, and the fill material can be a paint or dye substance and the soft gel capsules used in a paint ball gun or similar type applications.

The encapsulation machine produces two continuous flexible gelatin films/sheets/ribbons on either side of the machine that are subsequently joined together with the fill material injected therebetween via liquid injector 6 and volumetric feeder 3 as shown in FIG. 4 to form the soft gel capsules. The production of the two gelatin films are substantially the same for both sides of the encapsulation machine and are essentially mirror images of one another. A gelatin tank (not shown) provides a gelatin in a molten state that is fed through hoses into spreader boxes 19 that are located above casting drums 18. Spreader boxes 19 spread molten gelatin on rotating casting drums 18. Casting drums 18, as shown in FIG. 6, are internally liquid cooled and are externally air cooled. The cooling causes the molten gelatin that is spread on casting drums 18 to solidify and form flexible gelatin sheets. Each casting drum 18 produces a continuous flexible gelatin sheet that is used to form a portion of each capsule. Each of the casting drums 18 are driven by a servomotor which provide precise control of the rotation of casting drums.

The gelatin sheets formed on casting drums 18 flow through oil roller assemblies best seen in FIG. 6. The oil roller assemblies include several rollers. The two gelatin sheets flow into contact with wedge assembly 11, best seen in FIGS. 1, 3, 4 and 5, and then through co-acting rotary dies i.e., die 17 with an identical die on the other side. Wedge assembly 11 heats the sheets and supplies the fill material coming from liquid injector 6 and through volumetric feeder 3 as best shown in FIG. 3 between the two gelatin sheets that is encapsulated within the soft gel capsules produced by the rotary dies 17. The fill material is supplied to wedge assembly 11 from a fill mechanisms 6 and 7, shown in FIGS. 2 and 3. Fill supply mechanisms 6 and 7 include fill material hoppers 8 and 15 (FIGS. 1 and 6) that supplies the fill material to a pump assembly.

The two gelatin sheets travel between wedge assembly 11 and die assembly 17 (second die assembly not shown) and fill material is injected between the sheets by wedge assembly 11, shown in FIGS. 2 and 3. The rotary dies i.e., rotary die 17 and the other die not shown are driven by die shafts to rotate toward one another when producing soft gel capsules. The die shafts are driven by a servomotor 4. The mechanical link between the rotary dies provides synchronization of the two dies relative to one another during operation. The use of a mechanical linkage is advantageous in that it eliminates the need for another costly servomotor to drive the other die and the potential for non-synchronized operation due to programming or operator errors. Servomotor 4 enables precise control of the rate of rotation of the rotary dies and of the exact position of the dies at all times. Each die has a plurality of cavities thereon (see rotary die 17 in FIGS. 3 and 5) having suction means 10 so that the gelatin sheets are pushed into each mold and then the fill material is provided and subsequently the two sheets to be sealed together and cut along the cavities on the dies encapsulating the fill material therein and forming the soft gel capsules. The pressure between the rotary dies is pneumatically controlled by pneumatic cylinders which are controlled by a regulator.

The soft gel capsules produced in the encapsulation machine are transported to a conveyor not shown that runs along the front of the encapsulation machine. The conveyor transports the soft gel capsules to a dryer or similar type device for drying the soft gel capsules.

Referring now to FIGS. 2, 3 and 4 fill supply mechanisms 6 and 7 are used to fill the softgel capsule with liquid and microparticulate or nanoparticulate material. The fill supply mechanisms includes a liquid injector 6 and microparticle volumetric feeder 3. The drive mechanisms for the filling is driven by a servomotor 4 that allows precise control of the speed at which drive mechanism is operated and the position of drive mechanism. Servomotor 4 enables synchronization of fill mechanisms 6 and 7 with other components, such as the rotary dies without mechanical linkages or gears.

The microparticle or nanoparticle of the invention could be many different materials such as drugs, pigments or any solid that one desires to encapsulate. In a preferred embodiment of the invention, the microparticles or nanoparticles are pharmaceutically active ingredients.

To facilitate the understanding of all the drawings Applicant provides a glossary of each element associated with all the figures:

1. Vacuum Inlet
2. Rotary die (mold)
3. Volumetric feeder
4. Servomotor—Motor Synchronizer System
5. Servo Synchronizer System
6. Liquid Injection System
7. Microparticle or nanoparticle hopper
8. Microparticle or nanoparticle hopper
9. Liquid Injection Pump
10. Vacuum Chamber
11. wedge—segment 12. Medicine Pump Base
13. Medicine Dispenser Pump
14. Rotary die fastener—Mold fastener
15. Medicine hopper
16. Gelatin Film Guide roller
17. Rotary die—mold
18. Gelatin casting Drum—gelatin film-forming drum
19. Spreader box—gelatin dispenser box The contents of my copending non-provisional applications filed Jul. 18, 2011, and concurrently filed with this application and based on provisional applications No. 61/344,416 and 61/344,418 are incorporated by reference in their entirety as if they were individually denoted.

All patents, patent applications and publications cited in this application including all cited references in those applications and publications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What we claim is:

1. A method for forming softgel capsules having incorporated therein microparticles and/or nanoparticles, or said microparticles or nanoparticles dispersed in a suitable liquid, said method comprising:
   (a) feeding film sheets that have been heated by a wedge between a first die roll and a second die roll wherein each of the die rolls have capsule pockets in a plurality of rows and said capsule pockets have at least one orifice for application of suction;
   (b) applying suction while said film is in place in the capsule pockets;
   (c) applying through a synchronized volumetric feeder said microparticles and nanoparticles, or microparticles and nanoparticles dispersed in a suitable liquid or simultaneously filling with both liquid and microparticles or nanoparticles onto the film sheets overlying the die rolls at positions having the capsule pockets;
   (d) cutting the film sheets about the capsule pockets to form said soft gel capsules having microparticles or nanoparticles, or microparticles and nanoparticles dispersed in a suitable liquid; wherein said volumetric feeder is synchronized to rotate at the same tangential speed as the rotary dies and the feeder is synchronized through a synchronizing system that includes a servomotor thereby allowing the synchronization of the fill mechanisms with the roll dies without mechanical linkages or gears.

2. The method of claim 1 wherein said softgel capsules contain microparticles.

3. The method of claim 1 wherein said softgel capsules contain nanoparticles.

4. The method of claim 2 wherein said microparticles are bioactive pharmaceutical ingredients.

5. The method of claim 3 wherein said nanoparticles are bioactive pharmaceutical ingredients.

6. The method of claim 1 wherein said film sheet is a gelatin sheet.

7. The method of claim 1 wherein said film sheet is a polymer base sheet.

8. The method of claim 7 wherein said film sheet is a synthetic polymer base sheet.

9. The method of claim 1 wherein said film sheet is a cellulosic base sheet.

10. A soft capsule made by the process of claim 1.

* * * * *